US011140371B2

(12) United States Patent
Suzuki et al.

(10) Patent No.: US 11,140,371 B2
(45) Date of Patent: Oct. 5, 2021

(54) PROJECTION DEVICE

(71) Applicant: Panasonic Corporation, Osaka (JP)

(72) Inventors: Takashi Suzuki, Osaka (JP); Tomoyuki Saito, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 16/881,490

(22) Filed: May 22, 2020

(65) Prior Publication Data

US 2020/0288094 A1 Sep. 10, 2020

Related U.S. Application Data

(63) Continuation of application No. PCT/JP2018/043036, filed on Nov. 21, 2018.

(30) Foreign Application Priority Data

Nov. 27, 2017 (JP) .............................. JP2017-227164

(51) Int. Cl.
*A61B 34/20* (2016.01)
*A61B 5/00* (2006.01)
(Continued)

(52) U.S. Cl.
CPC .......... *H04N 9/3141* (2013.01); *A61B 90/36* (2016.02); *G02B 5/003* (2013.01); *G02B 27/141* (2013.01);
(Continued)

(58) Field of Classification Search
None
See application file for complete search history.

(56) References Cited

U.S. PATENT DOCUMENTS

| 5,772,593 A | 6/1998 | Hakamata |
| 2008/0004533 A1 | 1/2008 | Jansen et al. |

(Continued)

FOREIGN PATENT DOCUMENTS

JP 9-24053 1/1997

OTHER PUBLICATIONS

Extended European Search Report dated Nov. 16, 2020 in corresponding European Patent Application No. 18881790.2.
(Continued)

*Primary Examiner* — Patricia I Young
(74) *Attorney, Agent, or Firm* — Wenderoth, Lind & Ponack, L.L.P.

(57) ABSTRACT

A projection device includes an invisible image sensor, a projector, a visible image sensor, an imaging optical system, a light guide, and a light shield. The invisible image sensor captures an invisible light image of a subject. The projector projects a projection image based on the invisible light image onto the subject with visible light. The visible image sensor captures an image of the subject onto which the projection image is projected. The system includes a diaphragm. The light guide guides light to enter the system and light exited from the projector. The light shield is disposed at a space from the light guide. A diaphragm value is set so that a length difference between an optical length from a near point in a DOF of the system and an optical length from the light shield is longer than a front DOF from the subject.

10 Claims, 7 Drawing Sheets

(51) Int. Cl.
  *A61B 90/30*   (2016.01)
  *G02B 27/14*   (2006.01)
  *G03B 21/00*   (2006.01)
  *G03B 9/02*    (2021.01)
  *H04N 5/33*    (2006.01)
  *H04N 9/31*    (2006.01)
  *A61B 90/00*   (2016.01)
  *G02B 5/00*    (2006.01)

(52) U.S. Cl.
  CPC ................ *G03B 9/02* (2013.01); *H04N 5/33* (2013.01); *A61B 2090/366* (2016.02); *A61B 2090/3614* (2016.02)

(56) References Cited

U.S. PATENT DOCUMENTS

2018/0042692 A1* 2/2018 Kim .................... A61B 90/361
2018/0288404 A1* 10/2018 Ikehara ................ A61B 5/7445

OTHER PUBLICATIONS

International Search Report dated Jan. 22, 2019 in International (PCT) Application No. PCT/JP2018/043036.

* cited by examiner

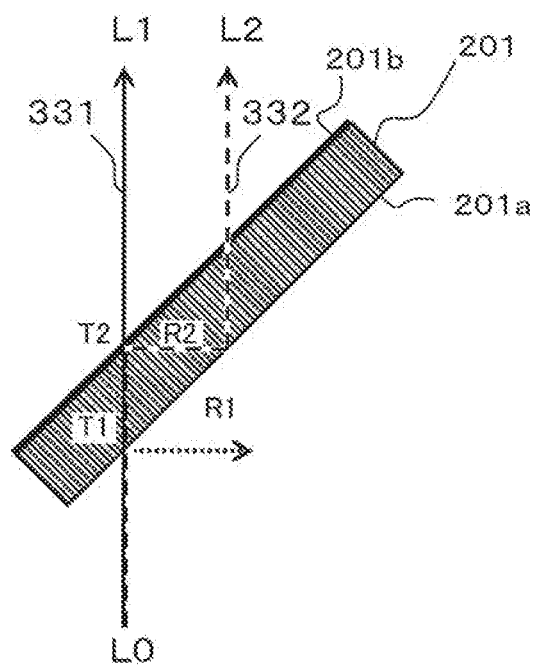

PROJECTION DEVICE

BACKGROUND

1. Technical Field

The present disclosure relates to a projection device for projecting an image generated based on a captured image of a subject.

2. Related Art

U.S. Patent Application Publication No. 2008/0004533 A discloses an optical imaging system for use in a medical field. The optical imaging system includes an electronic imaging device for capturing an image of a surgical site, a projector for projecting a visible light image resulting from image capturing of the surgical site under surgery, and an optical element for aligning an optical axis of the electronic imaging device with an optical axis of the projector. The optical imaging system captures a fluorescent image of the surgical site with the electronic imaging device, and projects, with the projector, a projection image for visualizing the captured fluorescent image.

SUMMARY

The present disclosure has an object to provide a projection device that enables accurate capturing of a visible light image for projecting a visible-light projection image generated based on a captured invisible-light image.

A projection device of the present disclosure includes an invisible image sensor, a projector, a visible image sensor, an imaging optical system, a light guide, and a light shield. The invisible image sensor is configured to capture an invisible light image indicating a subject in invisible light. The projector is configured to project a projection image onto the subject with visible light, the projection image being based on the invisible light image. The visible image sensor is configured to capture an image of the subject onto which the projection image is projected with visible light. The imaging optical system includes a diaphragm configured to regulate a quantity of light reaching the invisible image sensor and the visible image sensor. The light guide is configured to guide light to enter the imaging optical system and to guide light exited from the projector. The light shield is disposed at a space from the light guide. The diaphragm has a diaphragm value set so that a length difference between an optical length from a near point in a depth of field of the imaging optical system to the imaging optical system and an optical length from the light shield to the imaging optical system longer than a front depth of field from the subject, in a state where the subject is positioned within a range of the depth of field.

For projecting a visible-light projection image generated based on an invisible-light captured image, the projection device of the present disclosure enables accurate capturing of a visible light image, owing to the setting of the diaphragm.

BRIEF DESCRIPTION OF THE DRAWINGS

FIG. 7 is a view illustrating a multiplexed image in the surgery assistance system.

DESCRIPTION OF EMBODIMENTS

The following will describe embodiments of the present disclosure in detail with reference to the drawings as appropriate. However, unnecessarily detailed explanation may be omitted, occasionally. For example, detailed explanation of matters that have been already well known may be omitted, and explanation of matters that are substantially identical may not be repeated. This is for avoiding unnecessary redundancy in the explanations given below and for helping skilled persons understand the present disclosure.

The accompanying drawings and the following description are given by the applicants for helping skilled persons fully understand the present disclosure, and are not intended to limit the subject matters in the claims.

First Embodiment

The following will describe a surgery assistance system, which is a specific embodiment of a projection system including a projection device according to the present disclosure.

1. Configuration 1-1. Outline of Surgery Assistance System

Figure 1:
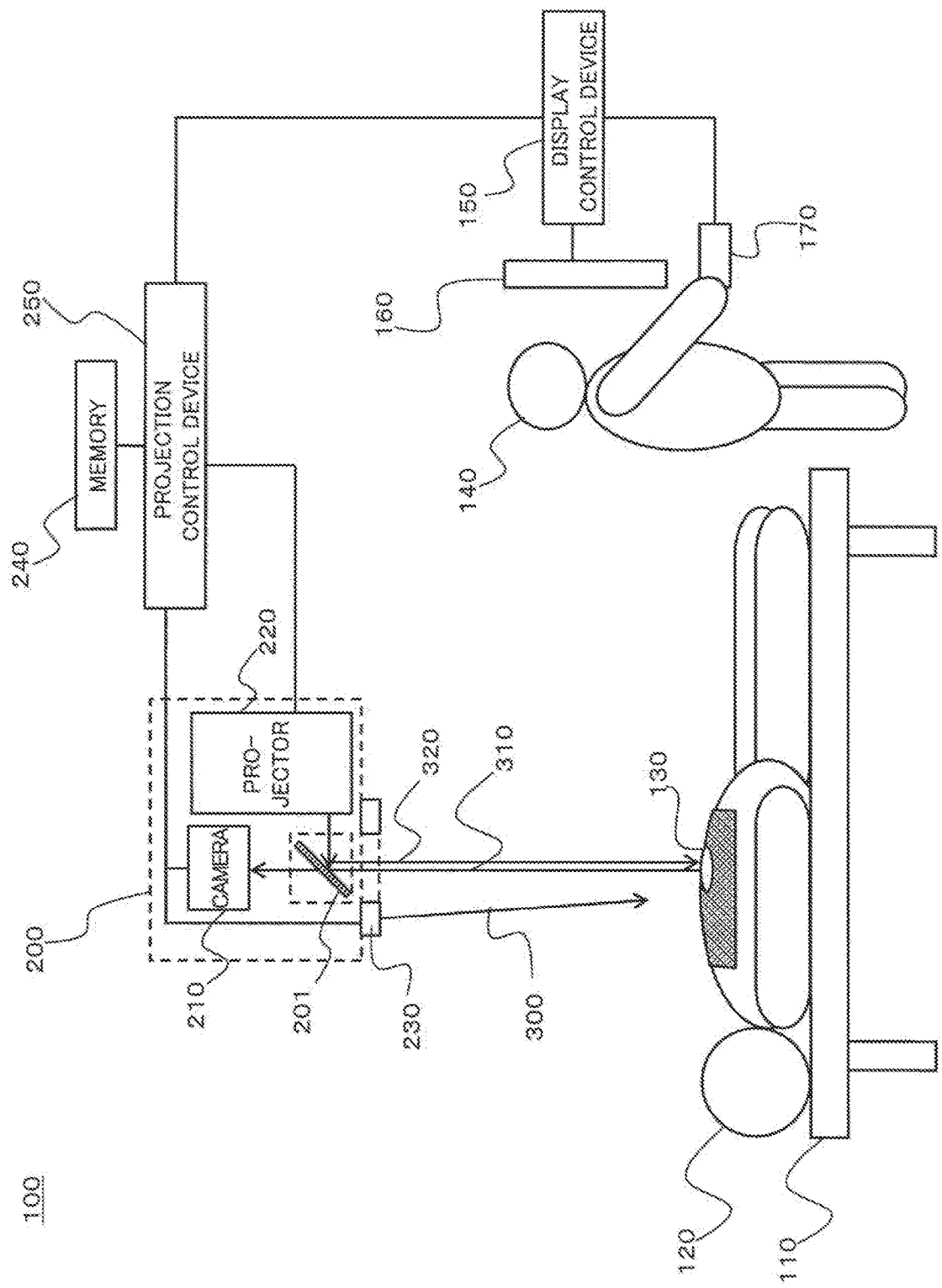
FIG. 1 is a schematic view showing a configuration of a surgery assistance system according to a first embodiment.

With reference to FIG. 1, the following will describe an outline of a surgery assistance system according to a first embodiment. FIG. 1 is a schematic view showing a configuration of a surgery assistance system 100 according to the first embodiment.

The surgery assistance system 100 includes a camera 210, a projector 220, and an excitation light source 230. The surgery assistance system 100 is a system for giving, with use of a projection image, a visual assistance in surgery performed on a patient by a doctor or the like in an operating room or the like. Before use of the surgery assistance system 100, a photosensitive substance is administered to a patient 120 who is to have surgery.

The photosensitive substance is a substance that emits fluorescence in response to excitation light. The photosensitive substance may be indocyanine green (ICG), for example. The present embodiment deals with a case where ICG is used as an example of the photosensitive substance. ICG emits fluorescence of a wavelength range from 800 nm to 860 nm, which is within an infrared region, in response to emission of excitation light of a wavelength range 760 nm to 780 nm and its neighboring values, which is within the infrared region.

When the photosensitive substance is administered to the patient 120, the photosensitive substance is accumulated in an affected part 130, where blood or lymph is stagnated. Thus, by detecting an area that emits fluorescence in response to emission of excitation light, it is possible to identify an area corresponding to the affected part 130.

Here, since the fluorescence emitted from the affected part 130 may be weak and/or may have a wavelength within or near an invisible region, a doctor or the like cannot visually identify the area corresponding to the affected part 130 even when visually observing the surgical site. In order to deal with this, the surgery assistance system 100 uses the camera 210 to identify the area corresponding to the affected part 130, from which fluorescence light 310 is emitted. In addition, in order to make the identified affected part 130 visible to a human, the projector 220 emits projection light 320, which is visible light, to the affected part 130. Consequently, a projection image that visualizes the area corresponding to the identified affected part 130 is projected. In this manner, it is possible to assist the doctor or the like who performs surgery in identification of the area corresponding to the affected part 130.

1-2. Configuration of Surgery Assistance System

With reference to FIG. 1, the following will describe a configuration of the surgery assistance system 100. The surgery assistance system 100 is installed in an operating room in a hospital for use. The surgery assistance system 100 includes a imaging irradiation device 200, a memory 240, and a projection control device 250.

In addition, although not illustrated, the surgery assistance system 100 includes a mechanism for relocating the imaging irradiation device 200. Examples of the mechanism encompass a driving arm mechanically connected to the imaging irradiation device 200 and casters of a pedestal on which a set of the surgery assistance system 100 can be placed. With the above mechanism, the imaging irradiation device 200 is positioned at a location perpendicularly above an operating table 110 on which a patient 120 is to be placed or at a location above the operating table 110 and inclined at a certain angle from a direction perpendicular to the operating table 110. The operating table 110 may include a driving mechanism capable of changing a height and an orientation of the operating table 110.

The imaging irradiation device 200, which includes the camera 210, the projector 220, the excitation light source 230, and a dichroic mirror 201 assembled integrally, is one example of a projection device. A configuration of the imaging irradiation device 200 will be described in detail later.

The memory 240 is a storage medium that the projection control device 250 accesses as needed in order to execute various calculations. The memory 240 is made of a ROM and a RAM, for example. The memory 240 is one example of a memory of the present embodiment.

The projection control device 250 comprehensively controls parts constituting the surgery assistance system 100. The projection control device 250 is electrically connected to the camera 210, the projector 220, the excitation light source 230, and the memory 240. The projection control device 250 is configured to output control signals for controlling the parts. The projection control device 250 is made of a central processing unit (CPU), for example. The projection control device 250 executes a predetermined program to achieve its function. The function of the projection control device 250 may alternatively be achieved by a specially designed electric circuit or a reconfigurable electric circuit (e.g., a field-programmable gate array (FPGA) or an application specific integrated circuit (ASIC)).

For example, the projection control device 250 performs various kinds of image processing on an image captured by the camera 210 to generate a video signal (image data) indicating a projection image. The projection control device 250 is one example of an image generating part of the present disclosure.

In the present embodiment, the surgery assistance system 100 includes a display control device 150, a monitor 160, and a mouse 170.

The display control device 150 is made of a personal computer (PC), for example. The display control device 150 is connected to the projection control device 250. The display control device 150 includes a CPU, for example. The display control device 150 performs image processing or the like to generate an image that is to be displayed on the monitor 160. The display control device 150 is one example of the image generating part of the present disclosure. The display control device 150 includes an internal memory (e.g., a ROM, a RAM), which is one example of the memory of the present disclosure.

The monitor 160 is made of a liquid crystal display or an organic electroluminescence (EL) display, for example. The monitor 160 has a display screen on which an image is displayed. The monitor 160 is one example of a display part of the present disclosure.

The mouse 170 is used by a user to input operation information to the display control device 150. The mouse 170 is one example of an adjuster of the present disclosure. Instead of or in addition to the mouse 170, the surgery assistance system 100 may include various kinds of adjusters, such as a keyboard, a touchpad, a touch panel, a button, and/or a switch.

During surgery, for example, an operator 140 (user) of the display control device 150 can check, on the monitor 160, the image captured by the camera 210. In addition, the operator 140 can adjust various settings on the projection image (e.g., a threshold value for a distribution of fluorescence intensities).

1-3. Configuration of Imaging Irradiation Device

Figure 2:
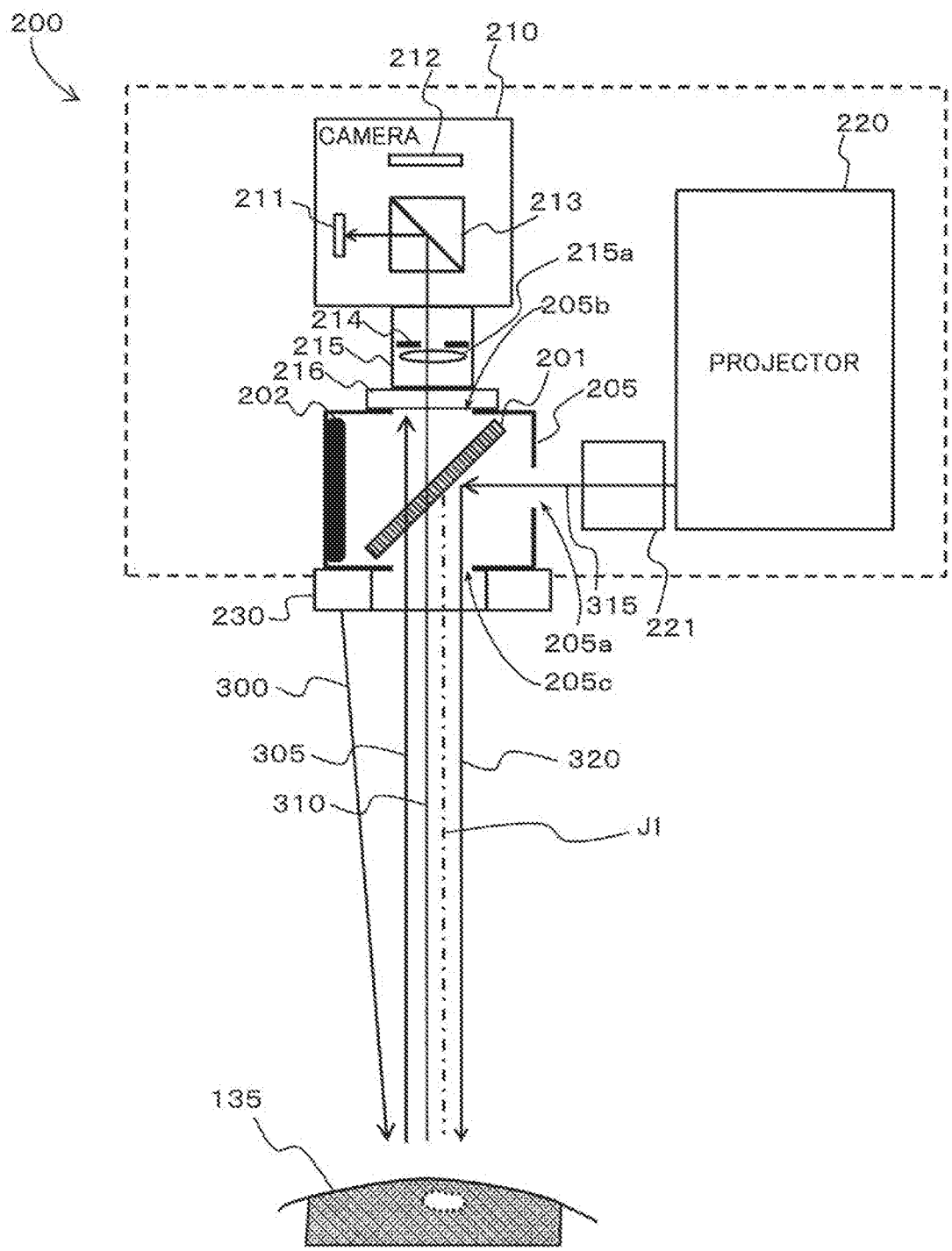
FIG. 2 is a block diagram showing a configuration of a imaging irradiation device in the surgery assistance system.

With reference to FIG. 2, the following will describe details of a configuration of the imaging irradiation device 200. FIG. 2 is a block diagram showing the configuration of the imaging irradiation device 200 in the surgery assistance system. The imaging irradiation device 200 includes the excitation light source 230, the camera 210, a zoom lens 215, an optical filter 216, the projector 220, a teleconversion lens 221, the dichroic mirror 201, and a light shield 202. The imaging irradiation device 200 is disposed at a location away from a subject, such as the surgical site 135, by a distance (height) of 1 m, for example.

The excitation light source 230 is a light source device for emitting excitation light 300 for causing a photosensitive substance to emit fluorescence. In the present embodiment, ICG is used as the photosensitive substance. Thus, the excitation light source 230 emits excitation light 300 of a wavelength band (e.g., within or near a range from 760 nm to 780 nm) including an ICG excitation wavelength. The excitation light source 230 is one example of an illuminator of the present embodiment. The excitation light source 230 is configured to turn on or off emission of excitation light 300 according to a control signal from the projection control device 250. The excitation light source 230 may be provided separately from the imaging irradiation device 200.

The camera 210 captures an image of a subject including, e.g., a surgical site 135 of the patient 120 to generate a captured image. The camera 210 transfers, to the projection control device 250, image data indicating the captured image thus generated. In the present embodiment, as illustrated in FIG. 2, the camera 210 includes an infrared ray (IR) sensor 211, an RGB sensor 212, and a prism 213.

The IR sensor 211 performs image capturing in infrared light (one example of invisible light) including a wavelength band of fluorescence from ICG, which ranges from 800 nm to 860 nm, to generate an invisible light image as the captured image. The IR sensor 211 is made of a complementary metal oxide semiconductor (CMOS) image sensor or a charge coupled device (CCD) image sensor, for example. The IR sensor 211 includes a filter for shielding light that is not infrared light, for example. The IR sensor 211 is one example of an invisible image sensor of the present embodiment.

The RGB sensor 212 is made of, e.g., a CMOS image sensor or a COD image sensor including RGB color filters provided to respective pixels. The RGB sensor 212 captures an image of visible light to generate a multi-color (RGB) visible light image. The RGB sensor 212 is one example of a visible image sensor of the present embodiment. The visible image sensor is not limited to the RGB sensor 212, and may alternatively be a monochrome image sensor.

Upon reception of incident light, the prism 213 passes a visible light component while reflecting an infrared light component. As illustrated in FIG. 2, the prism 213 is disposed between the zoom lens 215 and the RGB sensor 212. At a location close to a reflection surface of the prism 213, the IR sensor 211 is disposed. The prism 213 is one example of an internal optical system provided inside the camera 210. The internal optical system of the camera 210 is not limited to the prism 213. For example, an adjustment member of an optical path length may be disposed between the IR sensor 211 and/or the RGB sensor 212 and the prism 213.

The zoom lens 215 is attached to the camera 210, and converges external light into the camera 210. The zoom lens 215 regulates an angle of view (zoom value), a depth of field (DOF), a focus, and/or the like of the camera 210. The zoom lens 215 includes various lens elements including the lens 215a and a diaphragm 214. The diaphragm 214 is an aperture diaphragm, for example. The diaphragm 214 regulates a quantity of light that is to be converged by the zoom lens 215 according to a diaphragm value (e.g., an F-number) indicating the degree of opening.

The zoom value obtained by the zoom lens 215, the diaphragm value (F-number) of the diaphragm 214, and the like can be set externally, for example. The zoom lens 215 is one example of an imaging optical system of the present embodiment. The imaging optical system is not limited to the zoom lens 215. For example, the imaging optical system may include the internal optical system of the camera 210 and various external optical elements. Alternatively, the imaging optical system may be incorporated into the camera 210 as an internal optical system.

For example, the optical filter 216 is disposed at an incident surface of the zoom lens 215, as illustrated in FIG. 2. The optical filter 216 is made of a band-cut filter designed to shield certain wavelength components of incident light. The certain wavelength components ranges from 680 nm to 825 nm, including wavelengths from 760 nm to 780 nm of excitation light.

The projector 220 is a Digital Light Processing (DLP; registered trademark) projector, 3 Liquid Crystal Display (3LCD) projector, or a Liquid crystal on silicon (LCOS; registered trademark) projector, for example. The projector 220 emits projection light 315 to project a visible-light projection image generated based on a video signal from the projection control device 250. The projector 220 is one example of a projector of the present embodiment. The projector 220 includes a light source, an image forming device, and an internal optical system, for example.

The light source of the projector 220 is made of a laser diode (LD; semiconductor laser) or a light-emitting diode (LED), for example. The image forming device of the projector 220 includes a spatial light modulator such as a digital mirror device (DMD) or a liquid crystal display (LCD). The image forming device forms, on an image forming surface of the spatial light modulator, an image based on the video signal from the projection control device 250. The projector 220 spatially modulates light from the light source according to the formed image. Consequently, the projector 220 generates projection light 315, and emits the projection light 315 through the internal optical system.

The projector 220 may include a projection control circuit for achieving functions specific to the projector 220, such as trapezoid correction, a lens shift function, and/or the like. The above functions may be implemented by the projection control device 250. The projector 220 may be a laser scanning projector, and may include a micro electro mechanical systems (MEMS) mirror or a galvano mirror drivable in a scanning direction.

The teleconverter lens 221 is disposed so as to be optically coupled to the internal optical system of the projector 220. The teleconverter lens 221 extends a focal length of the projector 220 toward a telescopic side. In addition to or instead of the teleconverter lens 221, various optical elements may be disposed in an optical path extending from the projector 220 to the dichroic mirror 201.

The dichroic mirror 201 is one example of a light guide having optical characteristics of selectively passing or reflecting incident light according to the wavelength band of the light. For, example, the dichroic mirror 201 has 100% transmissivity and 0% reflectivity with respect to infrared light, each of which may have a tolerance error. In the present embodiment, a reflectivity and a transmissivity of the dichroic mirror 201 with respect to visible light are set so that visible light passes through the dichroic mirror 201 at a rate lower than the reflectivity with respect to visible light. Desirably, the transmissivity of the dichroic mirror 201 with respect to visible light is 5% or less. For example, the reflectivity (hereinafter, referred to as "R1") of the dichroic mirror 201 with respect to visible light is 99%, whereas the transmissivity (hereinafter, referred to as "T1") of the dichroic mirror 201 with respect to visible light is 1%.

Namely, in the configuration including the dichroic mirror 201, 5% or less of visible light can be captured by the RGB sensor 212. Alternatively, the configuration for capturing 5% or less of visible light can be achieved not only by the single dichroic mirror 201 but also by a combination of the dichroic mirror 201 and another member located on the optical path for image capturing. For example, in addition to the dichroic mirror 201, filters may be attached to the optical filter 216 and the prism 213. With this configuration, 5% or less of visible light may be captured in total.

The dichroic mirror 201 has two principal planes facing each other within a thickness of 5 mm or less, for example. As illustrated in FIG. 2, the dichroic mirror 201 is fixed at a location inside a casing 205, for example, such that the principal planes respectively face the teleconverter lens 221 disposed close to the projector 220 and the zoom lens 215 disposed close to the camera 210. The casing 205 has a light-guiding hole 205a for the projector 220, a light-guiding hole 205b for the camera 210, and a light-guiding hole 205c for the outside. In the dichroic mirror 201, one principal plane opposed to the other principal plane disposed close to the projector 220 has an anti-reflection (AR) coating, for example (as described later in detail).

According to the optical characteristics described above, the dichroic mirror 201 passes fluorescence light 310 or the like traveling toward the camera 210 through the zoom lens 215 and the like, while reflecting a most part (a half or more) of projection light 315 emitted from the projector 220, as illustrated in FIG. 2. The projection light 320 thus reflected is directed onto the surgical site 135. In the present embodiment, the dichroic mirror 201 guides light in such a manner that an optical axis of light entering the camera 210, such as fluorescence light 310 coming from the surgical site 135, and an optical axis of projection light 320 with which a projection image is projected on the surgical site 135 coincide with each other on an optical axis J1. Consequently, it is possible to reduce a positional displacement of the projection image generated based on the image captured by the camera 210.

In the present disclosure, a tolerance error may be set for the coincidence of the optical axes appropriately. For example, the optical axes may coincide with each other with a tolerance error. The tolerance error may be an angle within a range of ±5 degrees or a distance between the optical axes within a range of 1 cm. The optical characteristics of the dichroic mirror 201 may be set as appropriate according to the characteristics of fluorescence from the photosensitive substance that is used, for example.

The light shield 202 is provided to an inner wall of the casing 205, the inner wall being opposite to the projector 220 via the dichroic mirror 201. The light shield 202 is disposed in the vicinity of but at a space from the dichroic mirror 201 in the casing 205. The light shield 202 shields the dichroic mirror 201 from stray light and/or the like.

In the present embodiment, the light shield 202 is made of a black member having a reflectivity of 3% or less (e.g., 0.5%) with respect to visible light, for example. The black member is made of a light absorbing film or a blackened film that absorbs light entering the film, for example. The black member of the light shield 202 may be a sheet material or painting.

2. Operation

The following will describe operation of the surgery assistance system 100 according to the present embodiment.

2-1. Projecting Operation

Figure 3:
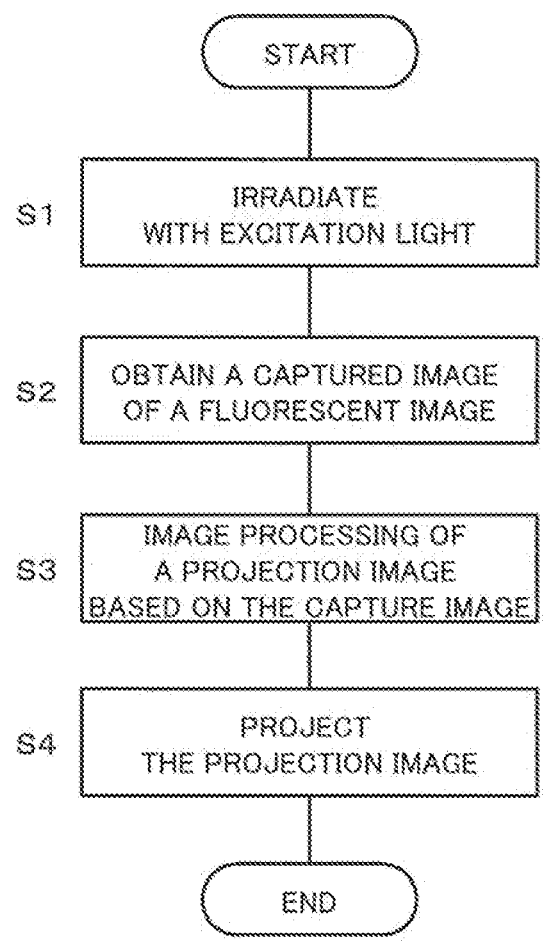
FIG. 3 is a flowchart for explaining projection operation of the surgery assistance system.
Figure 4A:
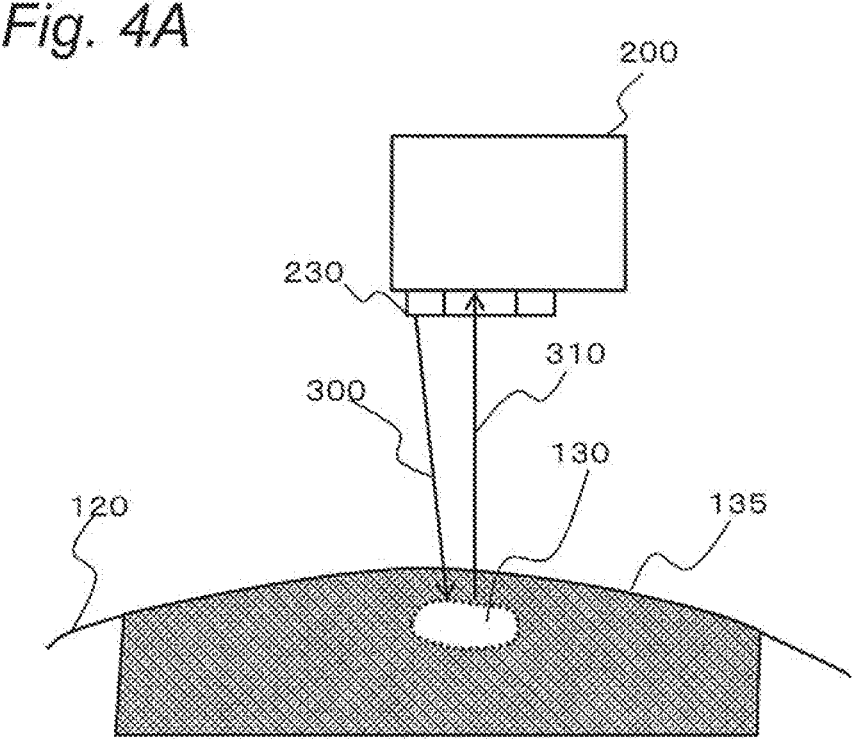
FIG. 4A is a view showing an example of a state of a surgical site observed before the projection operation is performed by the surgery assistance system.

With reference to FIGS. 3, 4A, and 43, the following will describe basic projecting operation of the surgery assistance system 100.

Figure 4B:
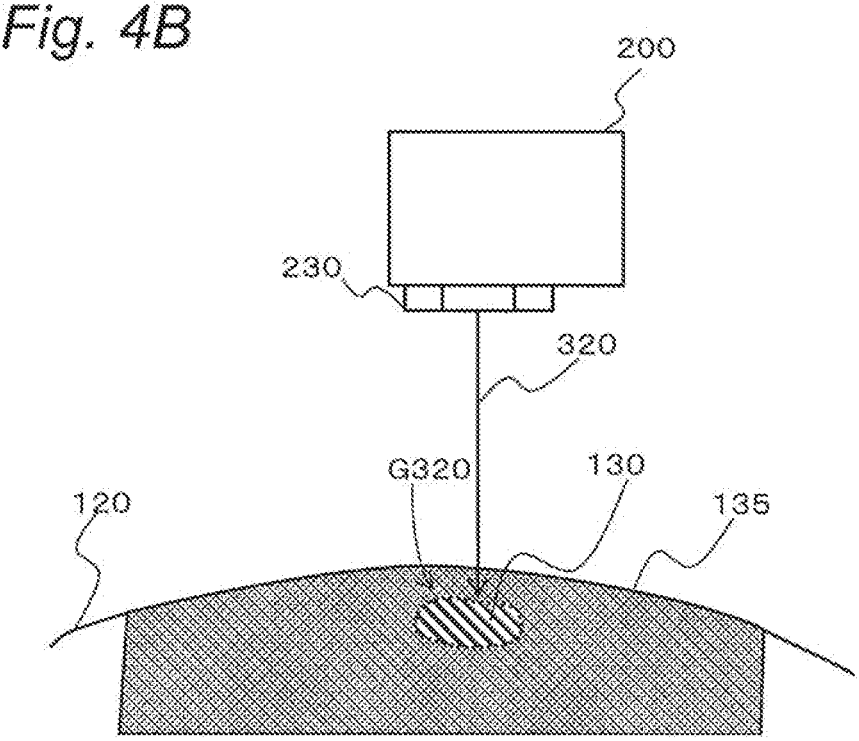
FIG. 4B is a view showing an example of a state of the surgical site observed during the projection operation of the surgery assistance system.

FIG. 3 is a flowchart for explaining projection operation performed by the surgery assistance system 100. FIG. 4A shows a state of the surgical site 135 observed before projection operation in a normal mode is performed by the surgery assistance system 100. FIG. 4B shows a state where the projection operation is performed on the surgical site 135 shown in FIG. 4A. The flowchart in FIG. 3 is executed by the projection control device 250.

In the flowchart in FIG. 3, the projection control device 250 first drives the excitation light source 230 to emit excitation light 300 to the surgical site 135 (S1), as shown in FIG. 4A. In response to emission of the excitation light 300, the affected part 130 in the surgical site 135 emits fluorescence. The fluorescence light 310 from the affected part 130 enters the imaging irradiation device 200.

In the imaging irradiation device 200, the fluorescence light 310 passes through the dichroic mirror 201, and then passes through the optical filter 216 of the camera 210, as shown in FIG. 2. Consequently, the camera 210 receives the fluorescence light 310 with the IR sensor 211. In this process, reflected light 305 that is the reflected excitation light 300 is shielded by the optical filter 216.

Next, the projection control device 250 captures an image of the surgical site 135, e.g., by controlling the camera 210, and obtains the captured image from the camera 210 (S2). The captured image obtained in step S2 includes a fluorescent image created as a result of reception of the fluorescence light 310 from the affected part 130.

Next, the projection control device 250 performs image processing for generating a projection image based on the captured image thus obtained (S3). The projection control device 250 generates an image corresponding to the fluorescent image in the captured image, and outputs the generated image as a video signal to the projector 220.

In the image processing in step S3, the projection control device 250 binarizes information indicating a distribution of received light intensities in the captured image based on a predetermined threshold value, for example. Consequently, the projection control device 250 identifies a region that is considered as a region of the fluorescent image in the captured image. Next, the projection control device 250 refers to various parameters stored in the memory 240, and performs various processes on the image including the identified region. Examples of the various processes include coordinate transformation such as shifting, rotation, and magnification/reduction as well as correction for image distortion. This results in generation of the image indicating a specific region corresponding to the fluorescent image in the captured image.

Next, the projection control device 250 controls the projector 220 to project the projection image that is based on the video signal thus generated (S4). Under control of the projection control device 250, the projector 220 generates the projection light 315 indicating the projection image that is based on the video signal from the projection control device 250, and emits the projection light 315 to the dichroic mirror 201 through the teleconverter lens 221 (see FIG. 2).

As illustrated in FIG. 2, the dichroic mirror 201 reflects (a major part of) the projection light 315, which is visible light, so as to emit projection light 320 along the optical axis J1. Consequently, as illustrated in FIG. 4B, the imaging irradiation device 200 emits the projection light 320 to the surgical site 135, so that a projection image G320 is projected on the affected part 130 in the surgical site 135. The projection image G320 is a monochrome image, for example.

The above processes are repeatedly performed at a certain cycle (e.g., 1/60 seconds to 1/30 seconds).

According to the above processes, the projection control device 250 identifies, based on the image captured by the camera 210, the region corresponding to the affected part 130 from which the fluorescence is emitted, so that the projection image G320 of visible light is projected from the projector 220 to the affected part 130. Consequently, the surgery assistance system 100 can visualize the affected part 130 that is difficult to be visually observed otherwise. With the surgery assistance system 100, a doctor and/or the like can visually check a state of the affected part 130 in real time.

In the foregoing description, the example where the projection image G320 is a monochrome image has been described. The projection control device 250 may generate a multi-tone projection image, e.g., by identifying the region of the fluorescent image in the captured image based on a plurality of threshold values. In addition, the projection control device 250 may generate the projection image in which the distribution of the received light intensities in the captured image are continuously reproduced. The projection image may be generated with multi colors or full colors.

2-2. Visible Image Capturing Function

Figure 5:
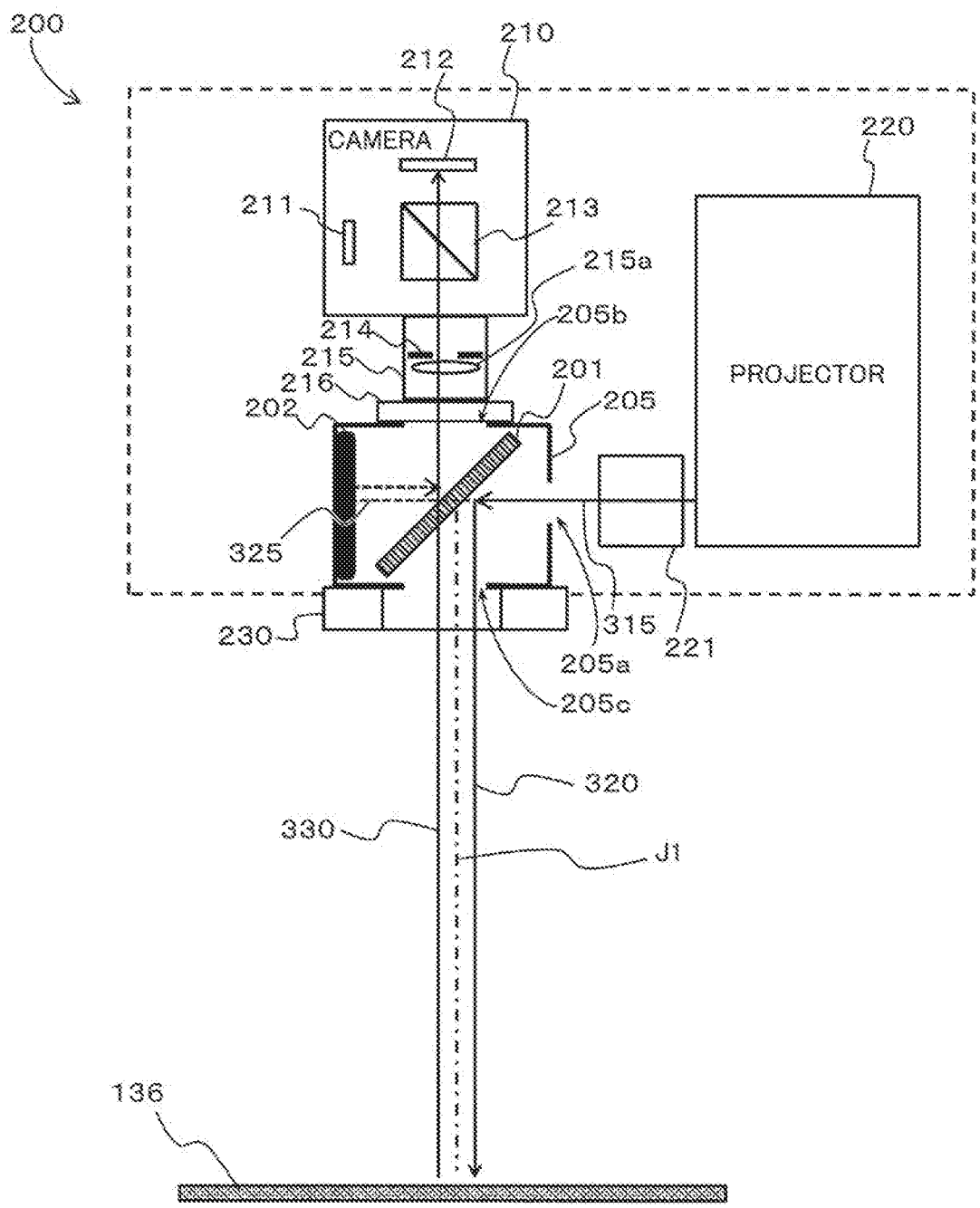
FIG. 5 is a view illustrating an optical path of visible light in the surgery assistance system.

In addition to the fluorescent image (S2 in FIG. 3) for generating the above-described projection image, the surgery assistance system 100 of the present embodiment captures a visible light image of a surgical site and/or the like. With reference to FIG. 5, the following will describe a visible image capturing function of the surgery assistance system 100.

FIG. 5 is a view showing an optical path of visible light in the surgery assistance system 100. Visible light 330 entering the imaging irradiation device 200 of the surgery assistance system 100 includes light that is external light reflected by the subject 136 such as the surgical site, light that is reflected projection light 320 and the like. The visible light 330 enters the imaging irradiation device 200 through the dichroic mirror 201.

The dichroic mirror 201 of the present embodiment passes a part of the entered visible light 330 so as to be incident on the zoom lens 215 through the optical filter 216. The optical filter 216 of the present embodiment passes the incident visible light 330 at a predetermined transmissivity. The zoom lens 215 tunes a luminous flux of the entered visible light 330 according to the zoom value and preset diaphragm value, and causes the visible light 330 to enter the camera 210.

In the camera 210, the prism 213 passes the visible light 330 entered thereto. The RGB sensor 212 receives the visible light 330 passed through the prism 213. Consequently, the RGB sensor 212 captures an image of the visible light 330 from the subject 136 or the like. The camera 210 outputs the visible light image resulting from the image capturing of the RGB sensor 212 to the display control device 150 and/or the projection control device 250, for example (see FIG. 1).

When infrared light of the fluorescence light 310 or the like enters the prism 213 (see FIG. 2), the prism 213 reflects the entered infrared light to guide the infrared light to the IR sensor 211. With the camera 210, it is possible to simultaneously capture the invisible light image with the IR sensor 211 and the visible light image with the RGB sensor 212.

The visible image capturing function is used to, e.g., display or record a state of a surgical site during surgery. For example, the display control device 150 (FIG. 1) displays a visible light image on the monitor 160 or records the visible light image in the memory 240 or the like. In addition, the display control device 150 may perform image processing of superimposing the invisible light image on the visible light image, for example. This can provide the surgery assistance system 100 with wide variety of display modes. The visible image capturing function is applicable also to correction of a positional displacement of the projection image G320 (FIG. 4B). For example, the projection control device 250 calculates a displacement amount of the projection image reflected on the visible light image, and performs a correction process on the projection image according to the displacement amount thus calculated.

The surgery assistance system 100 of the present embodiment incorporates the visible image capturing function with an optical axis of a visible image being coincident with an optical axis J1 for capturing a fluorescent image and projecting a projection image. Consequently, it is possible to enhance applicability of the visible light image to various uses by improving the accuracies in the image processing and the correction process on the visible light image, for example.

Here, with the surgery assistance system 100 incorporating the visible image capturing function in the above-described manner, new problems that are not expected in the system without the function are concerned. The following will describe problems by addition of the visible image capturing function.

In the present embodiment, a transmissivity T1 of the dichroic mirror 201 with respect to visible light needs to be higher than 0% although to be lower than a reflectivity R1 with respect to visible light but. Thus, at the dichroic mirror 201, leakage of the projection light 315 from the projector 220 may possibly occur. FIG. 5 shows one example of an optical path of stray light caused by the light leakage.

As shown in the example in FIG. 5, the projection light 315 from the projector 220 causes not only the projection light 320, which is reflected by the dichroic mirror 201 toward the subject 136, but also stray light 325, which passes through the dichroic mirror 201. The stray light 325 exits from the dichroic mirror 201 toward a wall surface of the casing 205 opposite of the projector 220. If the stray light 325 is reflected by the wall surface, the stray light 325 is to be incident on the dichroic mirror 201 from the opposite side of the projector 220. Then, the dichroic mirror 201 reflects at least part of the incident stray light 325, so that the stray light 325 enters the camera 210.

By the above-described stray light 325, a problem of deterioration in accuracy in capturing of a visible image is presumed to arise. In order to solve this, the present embodiment disposes the light shield 202 at a location which is inside the casing 205 and at which the light shield 202 would not interfere with the optical path of the visible light 330 and the like. Owing to the light shield 202, it is possible to reduce the total quantity of stray light 325 reflected inside the casing 205. In addition, with the light shield 202 made of a black member, it is possible to enhance contrast in the visible light image.

Here, assume a case where there exists adhered dust or a scratch on the inner wall of the casing 205, such as on the light shield 202. In such a case, it is concerned that a reflection image of the dust or the like caused by stray light 325 would be reflected in the visible light image, resulting in loss of the accuracy in capturing of the visible light image. In order to solve this, the present embodiment opens the diaphragm 214 of the zoom lens 215 to a degree with which the reflection image resulting from reflection of the stray light 325 disappears. The following will describe the setting of the diaphragm value of the diaphragm 214 in the present embodiment.

2-2-1. Setting of Diaphragm Value

Figure 6:
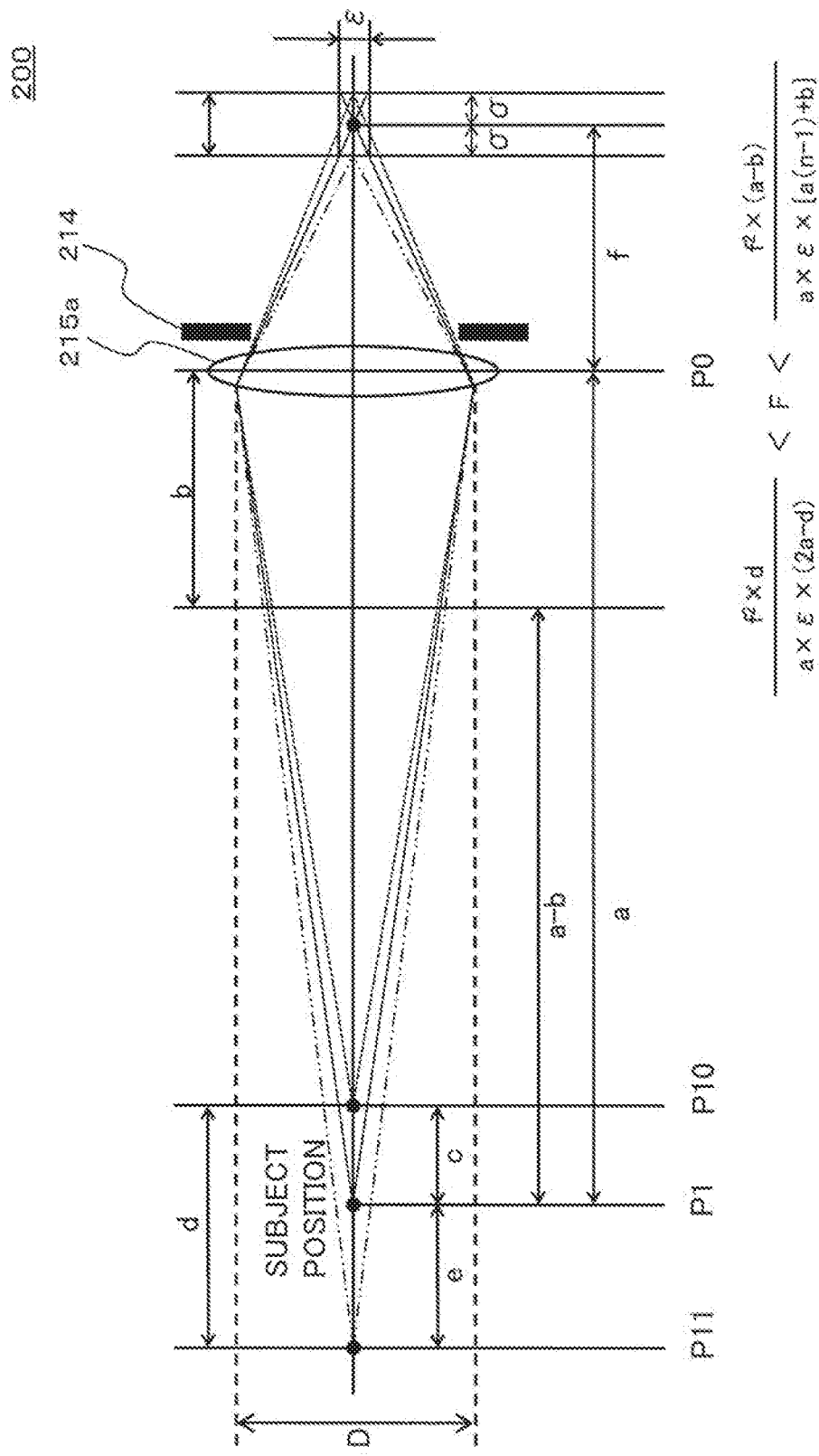
FIG. 6 is a view illustrating an optical length of light entering the imaging irradiation device.

With reference to FIG. 6, the following will describe setting of a diaphragm value of the diaphragm 214 of the present embodiment.

FIG. 6 is a diagram for explaining an optical length of light entering the imaging irradiation device 200 in the surgery assistance system 100. Hereinafter, instead of illustrating details of an imaging optical system of the camera 210 including various lens elements of the zoom lens 215, a lens 215a that is optically equivalent to the optical system is used for convenience of explanation.

By using the lens 215a, FIG. 6 schematically shows a range from a location of the subject 136 in the surgery assistance system 100 (FIG. 5) to a location of a focal point of the camera 210. FIG. 6 shows a subject distance a and a light shield distance b with the lens 215a as a reference. In addition, FIG. 6 shows an effective diameter D, a depth of field d, a front depth of field c, a rear depth of field e, a focal length f, a focal depth 2a, and a permissible circle of confusion E of the lens 215a.

The subject distance a is an optical length extending from a subject position P1, which indicates the position of the subject 136 (FIG. 5), to a principal point P0 of the lens 215a. The surgery assistance system 100 of the present embodiment is assumed to be used in a state where the subject 136 is positioned within a range of the depth of field d. Reflecting this, the subject position P1 is at a location between a near point P10, which is a closest point to the lens 215a in the depth of field d, and a far point P11, which is a farthest point from the lens 215a in the depth of field d.

The light shield distance b is an optical length extending from the light shield 202 (FIG. 5) to the principal point P0 of the lens 215a. For convenience of explanation, FIG. 6 shows the light shield distance b and the subject distance a on the same straight line.

The front depth of field c is a part of the depth of field d, the part extending from the subject position P1 to the near point P10. The rear depth of field e is a part of the depth of field d, the part extending from the subject position P1 to the far point P11.

In order to prevent from focusing on an object located within the light shield distance b, such as dust in the casing 205 in the surgery assistance system 100 (FIG. 5), a length from the near point P10 of the depth of field d to the principal point P0 of the lens 215a needs to be longer than the light shield distance b. That is, it is necessary to satisfy the following formula (1):

$$a-c>b \tag{1}$$

In the surgery assistance system 100 of the present embodiment, it is necessary not only to get out of focus in the light shield distance b but also to prevent a reflection image in the light shield distance b from being reflected in the visible light image. That is, the near point P10 of the depth of field d needs to be set adequately farther as compared with the above formula (1). This can be expressed in the formula (2) below:

$$a-b>n\times c \tag{2}$$

In the above formula (2), n is a number that is 1 or more, preferably a number that is 2 or more. In a case of n≥2, a length difference between the length (a−c), which is to the near point P10 of the depth of field d, and the light shield distance b can be equal to or more than the length of the front depth of field c.

Here, since the front depth of field c is a function of the F-number, the formula (2) can be expressed as the following formula (3) with use of the F-number (diaphragm value):

$$F<f^2\times(a-b)/[a\times\varepsilon\times\{(n-1)a+b\}] \tag{3}$$

The above formula (3) defines an upper limit of the F-number. The diaphragm 214 is set an opening degree so that the F-number is smaller than the upper limit defined by the right-hand side of the formula (3). In addition, a lower limit of the F-number of the diaphragm 214 is defined in view of the points below.

That is, the depth of field d in the surgery assistance system 100 is required to achieve a specification value do that is desirable for surgery assistance. The specification value $d_0$ of the depth of field d is a value in a range from 5 cm to 50 cm, for example. In order to achieve the specification value $d_0$ of the depth of field d, the following formula (4) is applied to the front depth of field c:

$$c>d_0/2 \tag{4}$$

In a similar manner to the above formulae (2) and (3), the formula (4) defines the lower limit of the F-number, as expressed by in the following formula (5):

$$F>f^2\times d_0/\{a\times\varepsilon\times(2a-d)\} \tag{5}$$

As an example of implementation of the surgery assistance system 100, the parameters may be assumed to be as below: the subject distance a=1300 mm, the light-shielding plate distance b=300 mm, the depth of field d (specification value $d_0$)=130 mm, the permissible circle of confusion ε=0.03 mm, and the focal length f=25.5 mm. In this case, since the right-hand side of the formula (3) is 10.4 and the right-hand side of the formula (5) is 0.9, it is found that a range of the F-number of the diaphragm 214 is from 1.0 to 10.0. The F-number of the diaphragm 214 is preferably near 2.0.

2-2-2. Multiplexed Image

The above-described incorporation of the visible image capturing function involves a problem of decrease in accuracy in image capturing due to reflection of a multiplexed image in the visible light image. For this problem, the surgery assistance system 100 of the present embodiment employs the configuration of the dichroic mirror 201 which can reduce reflection of a multiplexed image in the visible light image. With reference to FIG. 7, the following will describe a countermeasure of the present embodiment against the multiplexed image.

FIG. 7 is a view for explaining a multiplexed image in the surgery assistance system 100. Hereinafter, among two principal planes 201a and 201b of the dichroic mirror 201 shown in FIG. 7, the principal plane 201a closer to the subject 136 is referred to as a "front surface", and the principal plane 201b farther from the subject 136 is referred to as a "back surface".

The dichroic mirror 201 of the present embodiment is disposed such that the front surface 201a is closer to the projector 220 than to the camera 210 and the back surface 201b is closer to the camera 210 than to the projector 220 (see FIG. 5).

In the present embodiment, in order to implement the visible image capturing function, both of the reflectivity R1 and the transmissivity T1 of the dichroic mirror 201 with respect to visible light are set higher than 0%. Consequently, visible light from the subject 136 is internally reflected in the dichroic mirror 201, thereby being branched into a plurality of optical paths. This can result in generation of a multiplexed image. FIG. 7 shows two optical paths 331 and 332 that could generate a double image.

Referring to FIG. 7, the first optical path 331 is an optical path that linearly passes through the dichroic mirror 201 to form a primary visible light image of the subject 136. The second optical path 332 is an optical path that passes through the dichroic mirror 201 while being reflected by the back surface 201b and the front surface 201a inside the dichroic mirror 201. The second optical path 332 causes a double image, that is, a visible light image shifted from the visible light image based on the first optical path 331.

In order to reduce influence of the multiplexed image based on the second optical path 332 and the like, the present embodiment employs AR coating or the like applied to the back surface 201b of the dichroic mirror 201 so that a reflectivity R2 of the back surface 201b with respect to visible light is set lower than R1 which is a reflectivity of the main part of the dichroic mirror 201 (or a reflectivity of the front surface 201a).

Regarding the first optical path 331, visible light L0 from the subject 136 enters the dichroic mirror 201 through the front surface 201a at the transmissivity T1, and then exits from the dichroic mirror 201 through the back surface 201b at the transmissivity T2 without being reflected. Thus, the visible light L1 passed through the first optical path 331 can be expressed by the formula (6) below.

$$L1 = L0 \times T1 \times T2 \qquad (6)$$

On the other hand, regarding the second optical path 332, the visible light L0 from the subject 136 enters the dichroic mirror 201 through the front surface 201a at the transmissivity T1, and is then reflected by the back surface 201b at the reflectivity R2. The light reflected by the back surface 201b is further reflected by the front surface 201a at the reflectivity R1, and then exits from the dichroic mirror 201 through the back surface 201b at the transmissivity T2. Thus, the visible light L2 passed through the second optical path 332 can be expressed by the formula (7) below.

$$L2 = L0 \times T1 \times R2 \times R1 \times T2 \qquad (7)$$

According to the formulae (6) and (7), a quantity of light in the double image based on the second optical path 332 is smaller than a quantity of light in the primary visible-light image based on the first optical path 331 by a factor of R2×R1. Thus, even in a case where the reflectivity R1 of the dichroic mirror 201 (main part) with respect to visible light is 95% or more, it is possible to reduce the quantity of light in the double image to less than 1% of the quantity of light in the primary visible light, e.g., by setting the reflectivity of R2=1% for the back surface 201b.

The reflectivity R2 of the back surface 201b of the dichroic mirror 201 may be 5% or less. In order to avoid the multiplexed image, the dichroic mirror 201 desirably has a thin thickness (e.g., 5 mm or less). With the dichroic mirror 201 configured as above, it is also possible to reduce generation of the multiplexed image due to projection light from the projector 220.

3. Summary

As described above, the imaging irradiation device 200 that is one example of the projection device of the surgery assistance system 100 according to the present embodiment includes the IR sensor 211, the projector 220, the RGB sensor 212, the zoom lens 215, the dichroic mirror 201, and the light shield 202. The IR sensor 211 is one example of the invisible image sensor configured to capture an invisible light image indicating the subject 136 in invisible light. The projector 220 is one example of the projector configured to project a projection image G320 onto the subject 136 with visible light, projection image G320 being based on the invisible light image. The RGB sensor 212 is one example of the visible image sensor configured to capture an image of the subject 136 onto which the projection image G320 is projected with visible light. The zoom lens 215 is one example of the imaging optical system including the diaphragm 214 configured to regulate a quantity of light reaching the IR sensor 211 and the RGB sensor 212. The dichroic mirror 201 is one example of the light guide configured to guide light to enter the zoom lens 215 and to guide light exited from the projector 220. The light shield 202 is disposed at a space from the dichroic mirror 201. The diaphragm 214 has a diaphragm value set so that a length difference between an optical length (a–c) from a near point P10 of a depth of field of the zoom lens 215 to the zoom lens 215 and an optical length b from the light shield 202 to the zoom lens 215 longer than a front depth of field c of the subject 136, in a state where the subject 136 is positioned within a range of the depth of field (see the formula (2)).

For projecting a visible-light projection image generated based on a captured invisible-light image, the projection device configured as above enables accurate capturing of a visible-light image, while making a reflection image caused by dust and/or the like in the vicinity of the light shield 202 disappear.

In the present embodiment, the diaphragm value of the diaphragm 214 may be set so that the above length difference is longer than the depth of field d of the zoom lens 215 independently of the position of the subject 136. Owing to the setting by which the light shield distance b is farther away from the near point P10 of the depth of field d by the length of the depth of field d or more, it is possible to make the reflection image of the dust and/or the like disappear adequately.

In the present embodiment, the diaphragm 214 is adjusted (opened) within a range for which the depth of field d is equal to or more than a predetermined length (specification value do) (see the formula (4)). Consequently, it is possible to perform accurate capturing of an image of visible light, compatible with usability of the surgery assistance system 100.

In the present embodiment, the diaphragm value of the diaphragm 214 may be defined by an F-number that satisfies the formulae (3) and (5), where f denotes the focal length of the zoom lens 215, d denotes the depth of field, E denotes the permissible circle of confusion, a denotes the optical length between the subject 136 positioned within a range of the depth of field and the zoom lens 215, b denotes the optical length between the light shield 202 and the zoom lens 215, and n denotes a number which is 2 or more. Consequently, it is possible to perform accurate capturing of an image of visible light, compatible with usability of the surgery assistance system 100.

In the present embodiment, the light guide is the dichroic mirror 201 having a transmissivity T1 at which visible light passes through the dichroic mirror 201 at a rate lower than a reflectivity R1 with respect to visible light. The dichroic mirror 201 is disposed to pass and guide external light to the zoom lens 215 and to reflect light from the projector 220 to guide the light to the outside. The transmissivity T1 may be 5% or less.

In the present embodiment, the dichroic mirror 201 may have two principal planes 201a and 201b facing each other within a predetermined thickness. The dichroic mirror 201 is configured such that the principal plane 201b of the two principal planes 201a and 201b, which is closer to the zoom lens 215 than to the projector 220, has a reflectivity R2 at which visible light is reflected by the principal plane 201b, the reflectivity R2 being lower than a reflectivity R1 of the other principal plane 201a. Consequently, it is possible to reduce or prevent a multiplexed image that may otherwise be generated by the dichroic mirror 201, thereby improving the accuracy in capturing of a visible image. The reflectivity at which visible light is reflected by the principal plane 201b of the dichroic mirror 201, which is closer to the zoom lens 215, may be 5% or less.

In the present embodiment, the light shield 202 includes a black member having a reflectivity of 3% or less with respect to visible light. Consequently, it is possible to reduce a total quantity of stray light 325, thereby improving the contrast in the visible light image.

The projection device of the present embodiment may further include the excitation light source 230 configured to emit excitation light 300 that causes the subject 136 to emit fluorescence light 310, which is invisible light. The IR sensor 211 is configured to capture, as an invisible light image, an image of the subject emitting fluorescence. The projection device may further include the optical filter 216 that shields light of a wavelength band that is in common with that of the excitation light 300 and passes visible light and light of a wavelength band that is in common with that of the fluorescence light 310.

Other Embodiments

As described above, the first embodiment has been described as an example of the technique disclosed in the present application. However, the technique of the present disclosure is not limited to this, and is applicable also to other embodiments achieved by appropriately making modification, substitution, addition, and/or omission to the first embodiment. In addition, new embodiments can be made by combinations of the elements described for the first embodiment. The other embodiments of the present disclosure are illustrated below.

In the first embodiment, the dichroic mirror 201 has been described as one example of the light guide. The light guide of the present disclosure is not limited to the dichroic mirror 201. The light guide may be a polarizing prism, for example. In this case, the polarizing prism may be combined with a phase plate (¼λ plate) or a polarizing plate as appropriate. The light guide may be a dichroic mirror that reflects invisible light such as infrared light and passes visible light primarily. In this case, relative positions of the projector 220 and the camera 210 shown in FIG. 1 are interchanged.

In the above embodiments, infrared light is illustrated as one example of invisible light. However, the invisible light is not limited to infrared light, but may be ultraviolet light. The invisible light is not necessarily limited to light of a wavelength band in an invisible light range. The invisible light may include weak fluorescence of a red light region that is emitted in response to excitation light of a blue light region, for example. In this case, visible light used to form a projection image or a visible light image may be green light, for example.

In the above embodiments, an exemplary case where the projection device is applied to medical use is described. However, the display system of the present disclosure is not limited to this. For example, the projection device of the present disclosure is applicable to cases where it is necessary to perform a work on an object whose state changes are hard to be visually observed, such as an object in a construction site, a digging site, a building site, or a material processing factory.

Specifically, a fluorescent material may be applied, kneaded, or poured into the object whose state changes cannot be visually observed, such as an object in a construction site, a digging site, a building site, or a material processing factory, so that the object is set as a target whose image is to be captured with the camera 210.

As described above, the embodiments have been described as an example of the technique in the present disclosure. For this purpose, the accompanying drawings and detailed description have been provided.

Therefore, the elements in the accompanying drawings and the detailed description can include elements essential for solving the problems as well as elements shown to exemplify the technique and not essential for solving the problems. Thus, the non-essential elements should not be deemed as essential just because these elements are included in the accompanying drawings and the detailed description.

In addition, the embodiments described above are presented to exemplify the technique of the present disclosure.

Therefore, various modifications, substitutions, additions, and/or omissions may be made within a range of the claims.

A projection device of the present disclosure is applicable to cases where a work is to be performed on a subject whose state changes are difficult to be visually observed, such as a subject for medical use or a subject in a construction site, a digging site, a building site, or a material processing factory.

The invention claimed is:

1. A projection device comprising:
   an invisible image sensor configured to capture an invisible light image indicating a subject in invisible light;
   a projector configured to project a projection image onto the subject with visible light, the projection image being based on the invisible light image;
   a visible image sensor configured to capture an image of the subject onto which the projection image is projected with visible light;
   an imaging optical system including a diaphragm to regulate a quantity of light reaching the invisible image sensor and the visible image sensor;
   a light guide configured to guide light to enter the imaging optical system and to guide light exited from the projector; and
   a light shield disposed at a space from the light guide,
   wherein the diaphragm has a diaphragm value set so that a length difference between a first optical length from a near point in a depth of field of the imaging optical system to the imaging optical system and a second optical length from the light shield to the imaging optical system is longer than a front depth of field from the subject in a state where the subject is positioned within a range of the depth of field.

2. The projection device according to claim 1, wherein the diaphragm value is set so that the length difference is longer than the depth of field of the imaging optical system.

3. The projection device according to claim 1, wherein the diaphragm is adjusted within a range in which the depth of field is equal to or more than a predetermined length.

4. The projection device according to claim 1, wherein the diaphragm value is defined by an F-number that satisfies the formulae (1) and (2):

$$F < f^2 \times (a-b)/[a \times \varepsilon \times \{(n-1)a+b\}] \quad (1)$$

$$F > f^2 \times d/\{a \times \varepsilon \times (2a-d)\} \quad (2)$$

where f denotes a focal length of the imaging optical system, d denotes the depth of field, ε denotes a permissible circle of confusion, a denotes an optical length between the subject positioned within a range of the depth of field and the imaging optical system, b denotes an optical length between the light shield and the imaging optical system, and n denotes a number which is 2 or more.

5. The projection device according to claim 1, wherein the light guide is a dichroic mirror having a transmissivity at which visible light passes through the dichroic mirror at a rate lower than a reflectivity with respect to visible light, and
   the light guide is disposed to pass and guide external light to the imaging optical system and to reflect light from the projector to guide the external light to the imaging optical system and the reflected light from the projector to an outside.

6. The projection device according to claim 5, wherein the transmissivity is 5% or less.

7. The projection device according to claim 5, wherein the light guide has two principal planes facing each other within a predetermined thickness, and one of the two principal planes that is closer to the imaging optical system than to the projector has a reflectivity at which visible light is reflected by the one of the two principal planes, the reflectivity being lower than a reflectivity of the other of the two principal planes.

8. The projection device according to claim 7, wherein the reflectivity at which visible light is reflected by the one of the two principal planes of the light guide that is closer to the imaging optical system is 5% or less.

9. The projection device according to claim 1, wherein the light shield includes a black member having a reflectivity of 3% or less with respect to visible light.

10. The projection device according to claim 1, further comprising an excitation light source configured to emit excitation light that causes the subject to emit fluorescence light which is invisible light,
  wherein the invisible image sensor is configured to capture, as the invisible light image, an image of the subject emitting fluorescence light.

* * * * *